United States Patent [19]

Tzikas et al.

[11] 4,261,909

[45] Apr. 14, 1981

[54] PROCESS FOR THE REDUCTIVE REMOVAL OF HALOGEN ATOMS FROM ANTHRAQUINONES

[75] Inventors: Athanassios Tzikas, Pratteln; Jürgen Markert, Ettingen, both of Switzerland

[73] Assignee: Ciba-Geigy AG, Basel, Switzerland

[21] Appl. No.: 33,407

[22] Filed: Apr. 26, 1979

[30] Foreign Application Priority Data

Apr. 28, 1978 [CH] Switzerland .......................... 4648/78

[51] Int. Cl.$^3$ .................... C07C 103/7.5; C07C 97/24
[52] U.S. Cl. ..................................... 260/377; 260/378
[58] Field of Search .............. 260/369, 381, 377, 378, 260/649

[56] References Cited

U.S. PATENT DOCUMENTS 1,973,003 9/1934 Kunz et al. ........................... 260/381

Primary Examiner—Winston A. Douglas
Assistant Examiner—Raymond K. Covington
Attorney, Agent, or Firm—Wenderoth, Lind & Ponack

[57] ABSTRACT

A process for the reductive removal of halogen atoms from amino-, acylamino- or hydroxyanthraquinones, said halogen atoms being bonded in the α-position and/or ortho-position to amino, acylamino or hydroxyl groups, which comprises carrying out the reductive removal in basic medium with hydrazine or hydrazine derivatives.

7 Claims, No Drawings

PROCESS FOR THE REDUCTIVE REMOVAL OF HALOGEN ATOMS FROM ANTHRAQUINONES

The invention relates to a process for the reductive removal of halogen atoms from amino-, acylamino- or hydroxyanthraquinones, said halogen atoms being bonded in the α-position and/or ortho-position to amino groups, acylamino groups or hydroxyl groups, which comprises carrying out the reductive removal in basic medium with hydrazine or hydrazine derivatives.

Suitable starting materials are any anthraquinones which contain amino groups, acylamino groups and/or hydroxyl groups and one or more halogen atoms. The amino groups, acylamino groups, hydroxyl groups and halogen atoms can accordingly be in any position in the anthraquinone nucleus. In the process of the invention, those halogen atoms which are bonded in one α-position of the anthraquinone nucleus and/or are in the ortho-position to amino groups, acylamino groups or hydroxyl groups, are removed. On the other hand, halogen atoms which are bonded in the meta-position to amino groups, acylamino groups or hydroxy groups are not removed.

Examples of eligible amino and acylamino groups are: $-NH_2$, acetylamino and benzoylamino. The halogen atoms are chlorine, bromine and fluorine.

As starting compounds there are used preferably anthraquinones of the formula

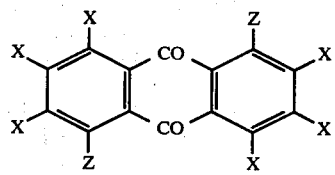

wherein one Z is the $-NH_2$ or $-OH$ group and the other Z is hydrogen, $-NH_2$ or $-OH$, and at least one X, which must be in the α-position and/or ortho-position to $-NH_2$ or $-OH$, is halogen, and the others, each independently of the other, are hydrogen or halogen.

The following anthraquinones may be cited as examples of starting materials for the process of the invention:
1-amino-4-chloroanthraquinone,
1-amino-2,4-dichloroanthraquinone,
1,8-diamino-4,5-dichloroanthraquinone,
2,6-diamino-1,3-dibromoanthraquinone,
2,6-diamino-1,5-dichloroanthraquinone,
1,4-diamino-2,3-dichloroanthraquinone,
1,4-diamino-5,8-dichloroanthraquinone,
1,5-diamino-4,8-dibromoanthraquinone,
1-amino-4-bromoanthraquinone,
2-amino-1-bromoanthraquinone,
1-amino-2-bromoanthraquinone,
2-amino-3-bromoanthraquinone,
1,4-diamino-2,5,8-trichloroanthraquinone,
1-amino-4,5-dichloroanthraquinone,
1-amino-2,3,4-trichloroanthraquinone,
1-amino-4,5,8-trichloroanthraquinone,
2,7-diamino-1,3,6,8-tetrabromoanthraquinone,
1,5-diamino-2,4,6,8-tetrabromoanthraquinone,
1,7-diamino-2,4,6,8-tetrabromoanthraquinone,
1,5-diamino-2,3,4,6,7,8-hexachloroanthraquinone,
1-acetylamino-2,3,4-trichloroanthraquinone,
1-benzoylamino-2,3,4-trichloroanthraquinone,
1,5-diamino-4,8-dihydroxy-3,7-dibromoanthraquinone,
1-amino-4-hydroxy-2,3-dibromoanthraquinone,
1-hydroxy-4-bromoanthraquinone,
1,4-dihydroxy-2-bromoanthraquinone,
1-hydroxy-5-chloroanthraquinone,
2-hydroxy-1-bromoanthraquinone,
1-hydroxy-4,8-dichloroanthraquinone,
1,4-dihydroxy-5,8-dichloroanthraquinone,
1,5-dihydroxy-4,8-dibromoanthraquinone,
1,4-dihydroxy-5,6,7,8-tetrachloroanthraquinone,
1,5-dihydroxy-2,4,6,8-tetrabromoanthraquinone,
1,8-dihydroxy-2,4,5,7-tetrabromoanthraquinone.

If an acylaminohaloanthraquinone is used as starting material, the acylamino group is saponified during the process to the $H_2N$ group.

If the anthraquinone nucleus contains several halogen atoms which are bonded in the α-position and/or ortho-position to an amino, acylamino or hydroxyl group (as do a number of the above compounds), then all these halogen atoms are removed by reduction in the process of the invention.

Reducing agents used in the process of the invention are hydrazine or hydrazine derivatives, for example: hydrazine, hydrazine hydrate, methyl hydrazine, ethyl hydrazine, phenyl hydrazine, hydrazinium chloride, hydrazinium dichloride, hydrazinium sulfate, hydrazinium bromide, benzenesulfonyl hydrazide. The preferred reducing agent is hydrazine hydrate.

The reaction is carried out in aqueous, aqueous-organic or organic medium. Particularly suitable organic media are solvents which are inert under the reaction conditions and are readily miscible with water.

The reduction is preferably carried out in water or protic solvents or in mixtures of water and protic solvents. Suitable solvents are in particular: water, methanol, ethanol, propanol, isopropanol, n-butanol, isobutanol, benzyl alcohol, diethylamine, triethylamine, aniline.

Instead of using pure homogeneous solvents it is also possible to use solvent mixtures, i.e. chiefly mixtures of water and protic solvents, such as water/methanol or water/ethanol. The reaction is preferably carried out in aqueous solution.

The reaction is carried out in a basic medium, preferably in a strongly basic medium, for example at a pH value of at least 10. The pH is preferably adjusted by addition of an alkali metal hydroxide, in particular sodium hydroxide or potassium hydroxide.

The reaction temperature can vary in any range compatible with the reactants, preferably between room temperature and the boiling temperature of the reaction mixture. It is particularly advantageous to begin the reaction at room temperature and to bring it to completion by raising the temperature to near that of the boiling range. An advantageous temperature range for the reaction is that between about 0° C. and 100° C. The reaction products can be isolated from the reaction mixture in a manner known per se. They are valuable intermediates for the manufacture of vat dyes, pigments and disperse dyes.

The invention is illustrated by the following Examples, in which parts and percentages are by weight unless otherwise indicated. The relationship between parts by weight and parts by volume is the same as that between gram and millilitre.

EXAMPLE 1

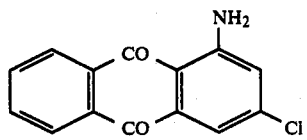

10 parts of 1-amino-2,3,4-trichloroanthraquinone are suspended at room temperature in 100 parts of 30% sodium hydroxide and then 15 parts of hydrazine hydrate are added to the suspension. The mixture is heated to 80° C. and kept at 80°–85° C. for 2 hours. Then the mixture is heated to 100° C. and kept for 1 hour at 100°–105° C. Subsequently 100 parts of water are added and the mixture is stirred at 80° C. for ½ to 1 hour. The reaction mixture is diluted with 500 parts of water and filtered. The filter cake is washed neutral with water and dried. Yield: 7.9 parts. A sample which is recrystallised from ethanol/dimethyl formamide (2:1) melts at 237°–240° C.

1-Amino-3-chloroanthraquinone is also obtained in good yield by repeating the above procedure using only 3 parts of hydrazine instead of 15 parts. The same compound is also obtained in equally good yield by repeating the above procedure using 11 parts of 1-acetylamino-2,3,4-trichloroanthraquinone or 13 parts of 1-benzoylamino-2,3,4-trichloroanthraquinone instead of 10 parts of 1-amino-2,3,4-trichloroanthraquinone.

EXAMPLE 2

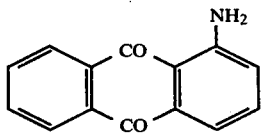

10 parts of 1-amino-2,4-dichloroanthraquinone are suspended at room temperature in 100 parts of 30% of sodium hydroxide, then 15 parts of hydrazine hydrate are added. The suspension is heated to 100° C. and stirred for 3 hours at 100°–105° C. Then 100 parts of water are added and the reaction mixture is stirred for about ½ to 1 hour at 80° C., diluted with 500 parts of water and filtered. The filter cake is washed neutral with water and dried, affording 7.4 parts of end product.

1-aminoanthraquinone is also obtained in high yield by repeating the above procedure using 5.5 parts of 1-amino-2,4-dibromoanthraquinone instead of 10 parts of 1-amino-2,4-dichloroanthraquinone.

EXAMPLE 3

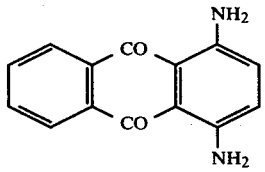

10 parts of 1,4-diamino-2,3-dichloroanthraquinone are suspended at room temperature in 100 parts of 15% potassium hydroxide and then 15 parts of hydrazine hydrate are added. The mixture is heated to 80° C. and kept for ½ hour at 80°–85° C. The mixture is then heated to 100° C. and kept for 3 hours at 100°–105° C. Then 100 parts of water are added and the reaction mixture is stirred for about ½ hour at 80° C., diluted with 500 parts of water and filtered. The filter cake is washed neutral with water and dried, affording 6.2 parts of end product. Recrystallisation from dimethyl formamide yields an analytically pure sample with a melting point of 263°–265° C.

The same end product is obtained in equally high yield by repeating the above procedure using 13 parts of 1,4-diamino-2,3-dibromoanthraquinone as starting material instead of 10 parts of 1,4-diamino-2,3-dichloroanthraquinone.

The same end product is also obtained in equally good yield by repeating the procedure of this Example, but carrying out the reaction at 105°–110° C. under a pressure of about 8 bar.

EXAMPLE 4

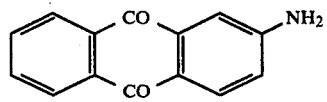

10 parts of 2-amino-3-chloroanthraquinone are suspended at room temperature in 100 parts of 15% sodium hydroxide, then 15 parts of hydrazine hydrate are added. The suspension is heated to 100° C. and stirred for 3 hours at 100°–105° C. Then 100 parts of water are added and the reaction mixture is stirred for about ½ to 1 hour at 80° C., diluted with 500 parts of water and filtered. The filter cake is washed neutral with water and dried.

Yield: 6 parts of end product. Recrystallisation from alcohol yields an analytically pure sample with a melting point of 302° C.

2-Aminoanthraquinone is also obtained in high yield by repeating the above procedure using 11 parts of 2-amino-3-bromoanthraquinone as starting material instead of 10 parts of 2-amino-3-chloroanthraquinone.

The same end product is likewise obtained in equally good yield by repeating the procedure of this Example using 12 parts of hydrazinium dichloride or 9 parts of hydrazinium chloride instead of 15 parts of hydrazinium sulfate.

EXAMPLE 5

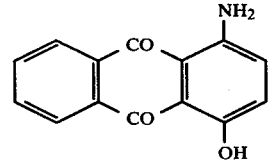

20 parts of 1-amino-4-hydroxy-2-bromoanthraquinone are suspended at room temperature in 200 parts of 15% sodium hydroxide and then 5 parts of hydrazine hydrate are added. The suspension is heated to 100° C. and stirred for 3 hours at 100°–105° C. under a pressure of about 5 bar. Then 100 parts of water are added and stirring is continued for about ½ to 1 hour at 80° C. The reaction mixture is then diluted with 500 parts of water and filtered. The filter cake is washed neutral with water and dried, affording 11 parts of 1-amino-4-hydroxyanthraquinone. Recrystallisation from alcohol yields an analytically pure sample with a melting point of 208° C.

1-Amino-4-hydroxyanthraquinone is also obtained in equally good yield by repeating the above procedure using 17 parts of 1-amino-4-hydroxy-2-chloroanthraquinone instead of 20 parts of 1-amino-4-hydroxy-2-bromoanthraquinone.

1-Amino-4-hydroxyanthraquinone is likewise obtained in equally good yield by repeating the procedure of this Example using a mixture of 180 parts of 15% sodium hydroxide and 20 parts of methanol, ethanol, isopropanol or propanol instead of 200 parts of 15% sodium hydroxide.

EXAMPLE 6

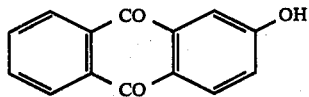

20 parts of 2-hydroxy-3-bromoanthraquinone are suspended at room temperature in 100 parts of 15% sodium hydroxide and then 5 parts of hydrazine hydrate are added. The suspension is heated to 100° C. and stirred for 3 hours at 100°–105° C. Then 100 parts of water are added and the reaction mixture is stirred for about ½ to 1 hour at 80° C., diluted with 500 parts of water and filtered. The filter cake is washed neutral with water and dried, affording 10.5 parts of 2-hydroxyanthraquinone. Recrystallisation from alcohol yields an analytically pure sample with a melting point of 304°–306° C.

EXAMPLE 7

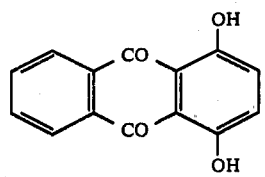

20 parts of 1,4-dihydroxy-2-bromoanthraquinone are suspended at room temperature in 200 parts of 15% sodium hydroxide and then 5 parts of hydrazine hydrate are added. The suspension is heated to 100° C. and stirred for 3 hours at 100°–105° C. Then 100 parts of water are added and the reaction mixture is stirred for about ½ to 1 hour at 80° C., diluted with 500 parts of water and filtered. The filter cake is washed neutral with water and dried, affording 10 parts of 1,4-dihydroxyanthraquinone. Recrystallisation from alcohol yields an analytically pure sample with a melting point of 192°–193° C.

What is claimed is:

1. A process for the reductive removal of halogen atoms bonded in the alpha-position and/or ortho-position to amino, acylamino or hydroxy groups from a halogen substituted anthraquinone which contains said amino, acylamino or hydroxyl groups, wherein the said halogen substituted anthraquinone is reacted with hydrazine or a hydrazine derivative in a basic solution of water or a mixture of water and protic solvent.

2. A process according to claim 1, wherein the reaction is carried out in aqueous solution.

3. A process according to claim 1, wherein the reaction is carried out in a mixture of water and protic solvents.

4. A process according to claim 1, wherein the pH value is adjusted by addition of an alkali metal hydroxide.

5. A process according to claim 1, wherein hydrazine hydrate is used as reducing agent.

6. A process according to claim 1, wherein 1-amino-2,3,4-trichloroanthraquinone is used as starting material.

7. A process according to claim 1, wherein 1-amino-2,4-dichloroanthraquinone or 1-amino-2,4-dibromoanthraquinone is used as starting material.

* * * * *